(12) United States Patent
Widder et al.

(10) Patent No.: US 7,702,473 B2
(45) Date of Patent: Apr. 20, 2010

(54) SUBMERSIBLE PORTABLE IN-SITU AUTOMATED WATER QUALITY BIOMONITORING APPARATUS AND METHOD

(75) Inventors: Mark W. Widder, Waynesboro, PA (US); Tommy R. Shedd, Middletown, MD (US); Mark W. Brown, Myersville, MD (US); Murray S. Swanson, Rockyridge, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/736,437

(22) Filed: Apr. 17, 2007

(65) Prior Publication Data

US 2008/0262739 A1 Oct. 23, 2008

(51) Int. Cl.
*G01N 11/00* (2006.01)
(52) U.S. Cl. ..................................................... 702/50
(58) Field of Classification Search .............. 702/23–26, 702/50, 19, 22, 30–33, 81, 108, 182; 73/61.41, 73/864.91; 119/224, 226, 231, 238
See application file for complete search history.

(56) References Cited

U.S. PATENT DOCUMENTS

| 6,058,763 | A | * | 5/2000 | Shedd et al. | ................ | 73/61.41 |
| 6,119,630 | A | * | 9/2000 | Lobsiger et al. | ............. | 119/238 |
| 6,988,394 | B2 | * | 1/2006 | Shedd et al. | ................ | 73/61.41 |
| 2008/0011061 | A1 | * | 1/2008 | Sihalla | ....................... | 73/64.56 |

FOREIGN PATENT DOCUMENTS

WO 95/03254 * 2/1995

OTHER PUBLICATIONS

Answers.com, Definition of in Situ, printed May 5, 2009.*

* cited by examiner

*Primary Examiner*—Michael P Nghiem
(74) *Attorney, Agent, or Firm*—Elizabeth Arwine

(57) ABSTRACT

A submersible biomonitoring system for monitoring water quality in situ includes a submersible chamber constructed of a di-electric material and sized to allow suitable signals from one or more aquatic organisms to be received by eliminating cross-talk between cells while allowing ambient conditions to be maintained inside the chamber. The aquatic organism exhibits ventilatory behavior and body movement sensitive to water quality which manifest as electrical signals picked up by electrodes and communicated to a pre-amplifier that conditions the signals for communication to a land-based amplifier and/or controller that is used to interpret the signals to determine when the water to which the organism is exposed has caused physiological stress to the organism.

10 Claims, 5 Drawing Sheets

SUBMERSIBLE PORTABLE IN-SITU AUTOMATED WATER QUALITY BIOMONITORING APPARATUS AND METHOD

I. FIELD OF THE INVENTION

The present invention relates generally to an apparatus and method for monitoring water quality. More particularly, the present invention relates to a submersible apparatus and in-situ method for monitoring water quality using the ventilatory behavior and body movement of aquatic organisms.

II. BACKGROUND OF THE INVENTION

Ventilatory responses are often some of the first prelethal symptoms exhibited by animals to environmental stressors. Continued, abnormal ventilatory behavior, such as rapid, shallow, or erratic breathing, can indicate physiological damage that may be irreversible. Changes in the ventilatory behavior of fish have been shown to be a reliable indicator of accidental toxic spills or "slugs" of pollutants in wastewater and drinking water systems. Accordingly, ventilatory biomonitoring systems can serve as an early indicator of impending damage to aquatic ecosystems and possible harm to humans.

The technological means are readily available to log and display ventilatory signals for subsequent analysis. As a result, there are a considerable number of studies that have examined ventilatory behavior of fish and other aquatic organisms. A large number of substances at lethal levels have been shown to elicit ventilatory responses relatively quickly. For many pollutants, a significant response was often generated in less than one hour of exposure to concentrations approaching the 96-hour LC50 (the concentration at which fifty percent of the organisms expire within 96 hours of exposure). Studies performed using subacutely toxic samples of effluents or individual pollutants (concentrations well below the reported LC50 concentration) often documented responses within one to ten hours of exposure.

Although a variety of organisms have been examined for this purpose, including crayfish, aquatic insect larvae, and bivalves, most research in aquatic ventilatory behavior has used freshwater fish species. This is largely because fish are generally more ecologically "visible" in their importance in aquatic systems and many species (particularly the salmonids and centrarchids) have large opercular flaps that yield relatively clear ventilatory signals for measurement and evaluation.

The ventilatory parameters in fish that have been shown to be affected by toxicity include ventilatory rate (opercular movement over time), depth of ventilation (amplitude), coughing or gill purge rate, and erratic episode frequency due to sudden movement of the organism. Most commonly, changes in just ventilatory rate, as opposed to the other parameters just mentioned, have been used as a bioindicator of toxic conditions. The depth of ventilation and gill purge or cough rate, however, have been reported to be more sensitive indicators of toxicity for some compounds.

Changes in ventilatory rate are often determined by manual examination of the peaks per unit area on a strip-chart recording. Depth of ventilation or signal amplitude is similarly measured from top to bottom of the waveform on the strip chart. Cough rate has been more difficult to determine even with manual examination of a strip chart as several different types of coughs may be present, with their own corresponding characteristic waveform pattern. Also, without the use of simultaneous video techniques, the actual occurrence of a cough is not always clear.

Another important aspect of water quality analysis is the ability to test water from a variety of sources at different locations. This is especially important when the water draining into a body of water comes from different sources. However, the nature and size of water monitoring equipment typically prevents such field testing.

The present inventors previously described a portable, land-based apparatus for automated biomonitoring of water quality in U.S. Ser. No. 10/774,639, filed Feb. 3, 2004, now U.S. Pat. No. 6,988,394, the entire contents of which are hereby incorporated by reference. As described in that application, a system for continuous, real-time comprehensive chemical analysis of drinking water for toxic chemicals is ideal for identifying water-borne threats. An automated fish biomonitoring system enhances detection capabilities for toxic and other chemicals by focusing chemical analyses on water quality changes that might otherwise go undetected. According to that application, the disclosed automated system preferably evaluates three fish behavior parameters, provides rapid notification of abnormal responses, and takes water samples for follow-up chemical analysis.

Today, the biomonitoring systems presently available include a mobile facility and a compact biomonitoring cabinet of the type described in U.S. Pat. No. 6,988,394. The mobile facility is somewhat large, heavy and cumbersome to transport. While the biomonitor cabinet greatly reduces size and weight requirements, it still requires a fixed facility for installation and use.

In order to minimize the equipment and need for a fixed facility, some prior artisans have suggested use of a submersible, or in-situ, monitoring apparatus. As will be appreciated, a submersible or in-situ monitoring apparatus would eliminate the need for pumps, manifolds, temperature controls, motors, etc. that are necessary for sampling, transporting, conditioning and analyzing water with existing prior art biomonitoring systems. An in-situ application would be particularly advantageous with fish farms or the like where real time monitoring of conditions that pose a threat to fish could be detected almost immediately so corrective action could be taken to avoid loss of an entire crop of fish. However, the construction of a submersible or in-situ monitoring device has proven problematic. For reasons not easily explained, there exists a physical phenomenon whereby signals generated by fish in a submersed monitoring chamber are incapable of being received in a quality sufficient for biomonitoring. Most prior artisans agree that pursuit of a submersible monitoring chamber is a lost cause due to this inability to receive suitable signals from fish in a submersed exposure chamber.

Accordingly, there exists a long-felt, yet unresolved need in the art for a submersible biomonitoring chamber. The present invention meets this need by the provision of novel equipment and methods of monitoring water quality through deployment of fish monitoring chambers directly in the body of water to be monitored. This submersible system not only overcomes the need for a fixed facility, but also fulfills the long-felt need in the art for in-situ water quality biomonitoring.

III. SUMMARY OF THE INVENTION

The present invention overcomes the practical problems described above and provides additional advantages as well. The present invention is based, in part, on the discovery that the use of specifically-proportioned biomonitoring chambers made of a dielectric material allows for receipt of signals of sufficient quality for biomonitoring water quality in-situ.

Accordingly, one object of the present invention is to provide a submersible apparatus for automated biomonitoring of water quality. A related aspect of the invention is to provide embodiments of the submersible system that eliminate the need for pumps, tubing, temperature control, filtration, water manifolds, and the like currently used for monitoring water quality. One advantageous feature of at least one embodiment of the invention is that the submersible design overcomes the affects caused by water loss due to mechanical failure found in land-based systems. Another advantageous feature of at least one embodiment of the invention is the reduction in power requirements to run a submersible system as opposed to a land-based system requiring pumps and the like. In accordance with one embodiment of the invention, the power requirement is reduced from several amps to less than 0.5 amps for 16 amplifiers. Accordingly, an object of the invention is to provide a submersible system for monitoring water quality that allows for solar powered operation.

An additional related aspect of the invention is to provide a low cost alternative to land-based monitoring systems, wherein the savings in having reduced architecture to run the system allows for multiple monitoring sights to be deployed at the same price as it would cost to operate one fixed sight. An advantageous feature of this aspect of the invention is use of the system to deploy an in-stream network of monitoring units that could track developing toxic conditions in a watershed or along the length of a stream or river. As will be appreciated, having numerous data collection areas in a body of water provides substantial benefits in detecting, pinpointing, and remediating a source of contamination over a single fixed facility.

Another object of the present invention is to configure a submersible ventilatory chamber design that would provide electrical sensing characteristics similar to those of non-submersible ventilatory chambers. According to this object of the invention, a feature of the invention is the configuration of a submersible chamber that optimizes signal quality while minimizing electrical cross talk between cells. According to this object of the invention, another feature of the invention is the configuration of a submersible chamber that also maintains the systems' ambient sensing capabilities.

These and other objects and advantages of the present invention may be realized by one or more of the embodiments described herein. Many of these objects are met by a submersible portable system for monitoring and evaluating water quality including an exposure chamber for housing an aquatic organism made out of a dielectric material. The chamber is preferably configured of specific dimensions to achieve reliable signal transmission and reception. In other words, the chamber must not be too short or it will suffer from too much cross-talk between chambers and must not be too long or it will have insufficient and unreliable ambient sensing capabilities.

According to a presently preferred embodiment, the submersible chamber comprises a chamber including eight chamber cells. Each chamber cell is configured to hold an aquatic species. Each cell includes end caps to prevent the aquatic species from exiting the chamber. The end caps further include a plurality of openings that allow water to flow through the chamber in a manner akin to the natural distribution or current in the body of water being monitored. Each cell further includes electrodes for receiving biofeedback signals from the aquatic organism in the cell. The electrodes then communicate the signals to a preamplifier attached to, or integral with, the chamber. The chamber also preferably includes an umbilical tether of coaxial cable extending from the pre-amplifier to an above water amplifier where the signal is amplified and communicated to a controller for analysis and processing to determine water quality. In a preferred embodiment, the system is powered by a solar battery which further enhances its deployability.

More specifically, the electrodes quantify the generated electrical signals into data and output the data as a behavioral signal. Electrical signals picked up and quantified by the electrodes are then preferably supplied to an automatic controller, which determines a plurality of ventilatory and body movement parameters based on the signals from the electrodes. The controller compares the parameters with corresponding thresholds to determine when the water to which the organism is exposed has caused physiological stress to the organism.

In addition, the system preferably provides electrical signals to the controller or similar device for determining a wide variety of ventilatory and body movement parameters. In a preferred embodiment, the apparatus provides electrical signals for determining at least the ventilatory frequency, the average ventilatory depth, and the cough rate of the organism.

The system may also include accessories for analyzing water quality such as a water quality sensor configured to detect a characteristic of the ambient water. The controller is preferably responsive to the water quality sensor by comparing the water characteristic with the corresponding behavioral signal to determine when a change in one or more of the ventilatory parameters occurred at the approximate time that a change in water characteristic occurred.

The system may further include various devices operative in response to a determination of a water quality problem by the controller. For example, it may include an alarm mechanism for generating an alarm in the event of an indication of a problem with the water quality. The system may also include architecture for wireless communication of results, information, and instructions to receivers associated with a command center or other deployed systems.

Another advantageous feature of the invention is the use of an aerator to provide oxygen to the pens to aid the survival of their occupants in the event of an incident affecting water quality. Any suitable aeration device or method may be configured for use with the present invention by one of ordinary skill in the art.

Another aspect of the present invention relates to a method of evaluating water quality including the steps of submersing an exposure chamber housing at least one aquatic organism in a body of water, detecting electrical signals generated by the aquatic organism, and measuring a plurality of ventilatory parameters of the aquatic organism based on the electrical signals.

The monitoring and determination of ventilatory and body movement parameters of an aquatic organism by a submersible system as taught in the present invention provides for continuous, around-the-clock monitoring of water quality with reliable in-situ results. As will be appreciated, such results are not otherwise possible with current non-in situ methods of biomonitoring. The in situ nature of the present invention also allows for the use of a plurality of ventilatory and body movement parameters to provide more reliable and accurate measurements of water quality than prior art systems.

Moreover, the in situ nature of the present invention also allows for deployment directly in a fish farm, thereby providing the most accurate and immediate determination of the existence of stress to a fish crop. Rather than sampling water and testing its quality, the in situ system of the present invention provides real time ambient testing of water quality. The present invention may also be readily integrated with effluent control systems for wastewater treatment plants, factories, and other possible sources of pollutants to provide real time ambient water quality monitoring, thereby providing a detection capability for inadvertent or intentional toxic contamination to a water source. As will be appreciated, such contamination could otherwise go undetected without the present invention until human health is affected and traced to the source of contaminated drinking water.

In addition, the exposure chamber of the present invention provides improved biomonitoring of aquatic organisms due to the fact it may be disposed in-situ and thus not susceptible to inadequate mixing of the water prior to organism exposure, water stratification within the chamber, inadequate artificial temperature control, or water loss common in prior art above-ground monitors. Because the method of the present invention is easily transportable and designed for deposit into the body of water to be monitored, it may be quickly implemented in a variety of environments for immediate analysis, unlike existing biomonitoring methods.

In addition to the foregoing, the present invention also readily lends itself to deployment as a network of in situ monitoring stations throughout a body of water. In such deployment, the various stations collect separate data which may be used to determine the extent of contamination, the path of contamination, and ultimately, the source of contamination.

In the following description, reference is made to the accompanying drawings, and which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known methodology and/or functional equivalents may be made without departing from the scope of the invention.

Given the following enabling description of the drawings, the novel submersible biomonitoring systems of the present invention and their various respective advantageous features should become evident to a person of ordinary skill in the art.

IV. BRIEF DESCRIPTION OF THE DRAWINGS

V. DETAILED DESCRIPTION

As previously mentioned, the present invention is based, in part, on the discovery that the use of specifically-proportioned chambers and cells made of a dielectric material allows for receipt of signals of sufficient quality for biomonitoring water quality in-situ. While the present invention will be described in connection with a submersible in situ chamber for biomonitoring water quality, it will be readily apparent to one of ordinary skill in the art that the present invention can be applied to a multiplicity of fields and uses, including other areas where cross-talk or the inability to assure reliable ambient conditions are needed. Furthermore, while the present invention will be described in connection with the use of certain specific aquatic species, one of ordinary skill in the art will recognize the interchangeability and ease to which the device can be used with alternative species. Finally, while the present invention will be described in connection with a single submersible chamber having eight individual holding pens, one of ordinary skill in the art will recognize that any suitable configuration or number of chambers and cells are within the scope of the invention.

Figure 1:
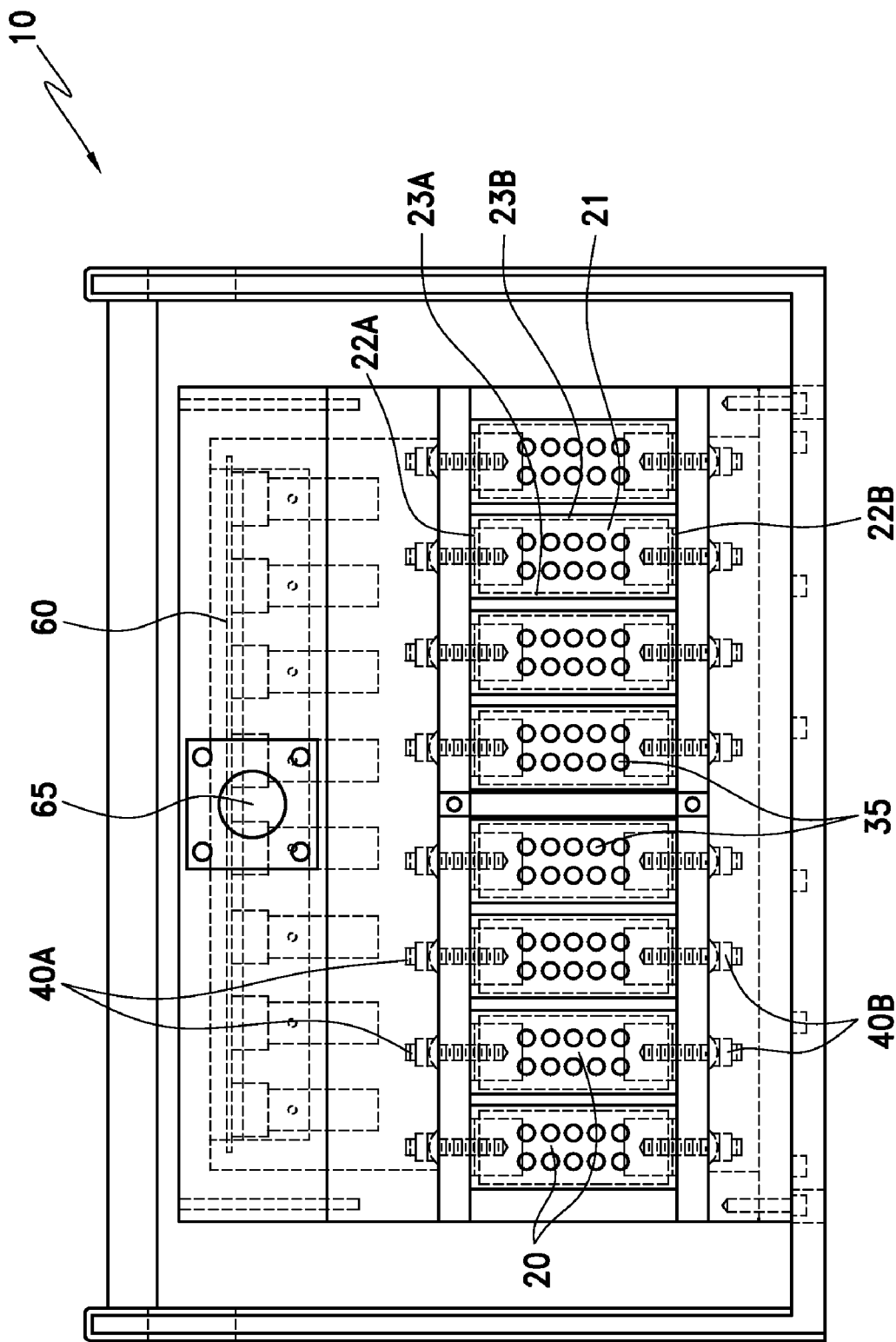
FIG. 1 is a front view of an embodiment of a submersible biomonitoring chamber according to the invention.
Figure 2:
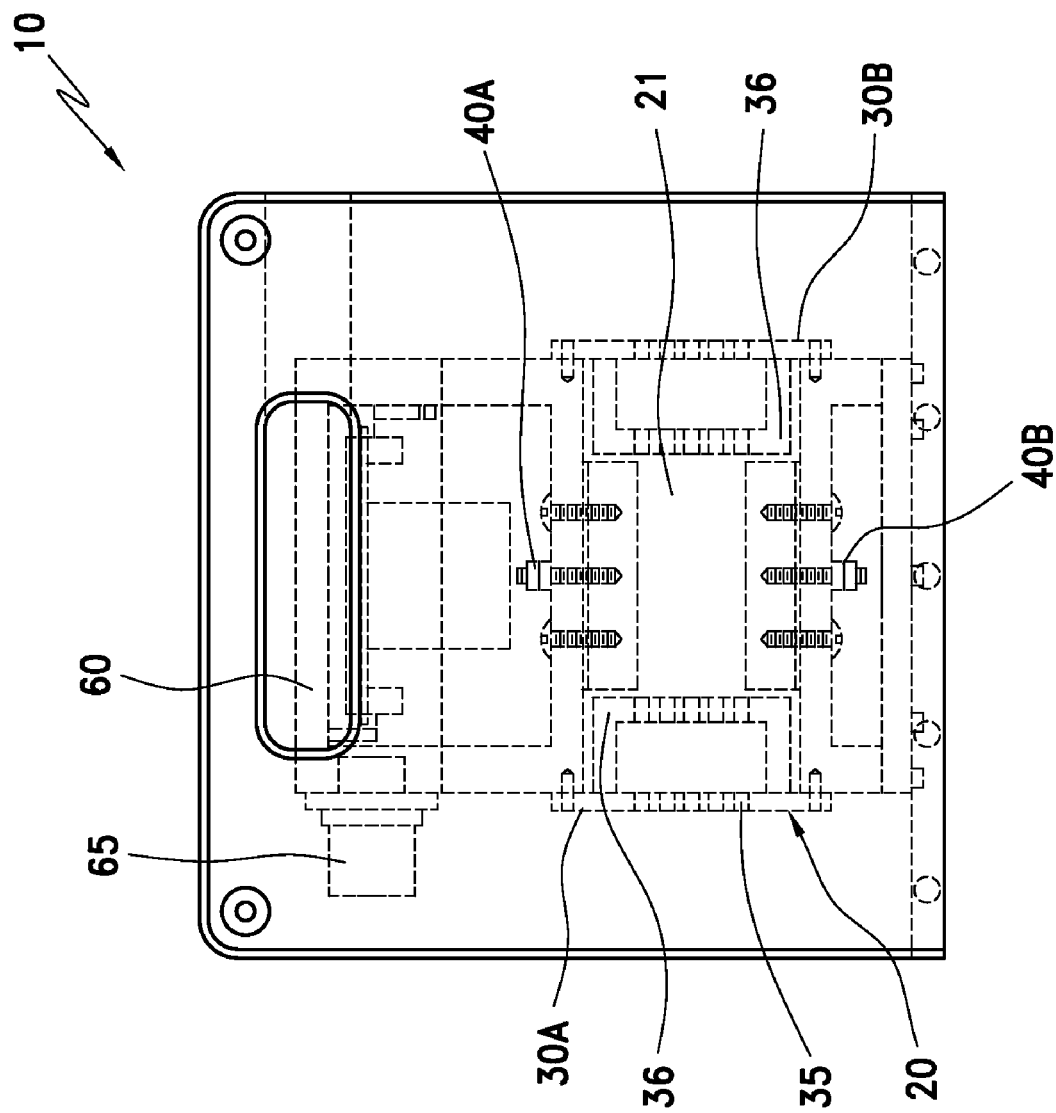
FIG. 2 is a side view of an embodiment of a submersible biomonitoring chamber according to the invention.
Figure 3:
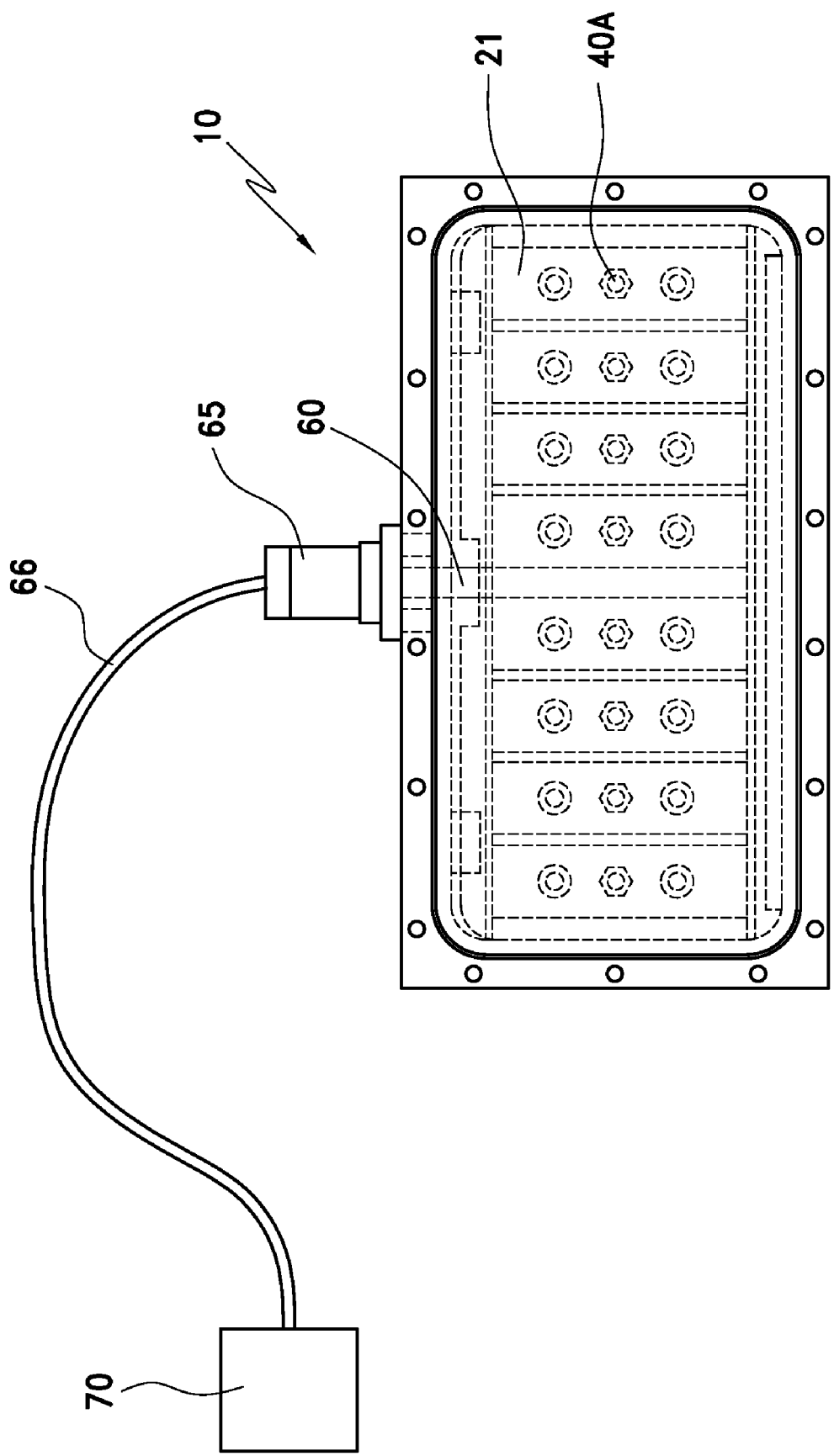
FIG. 3 is a top view of the chamber cells or holding pens for aquatic species of the submersible chamber of FIG. 1.
Figure 4:
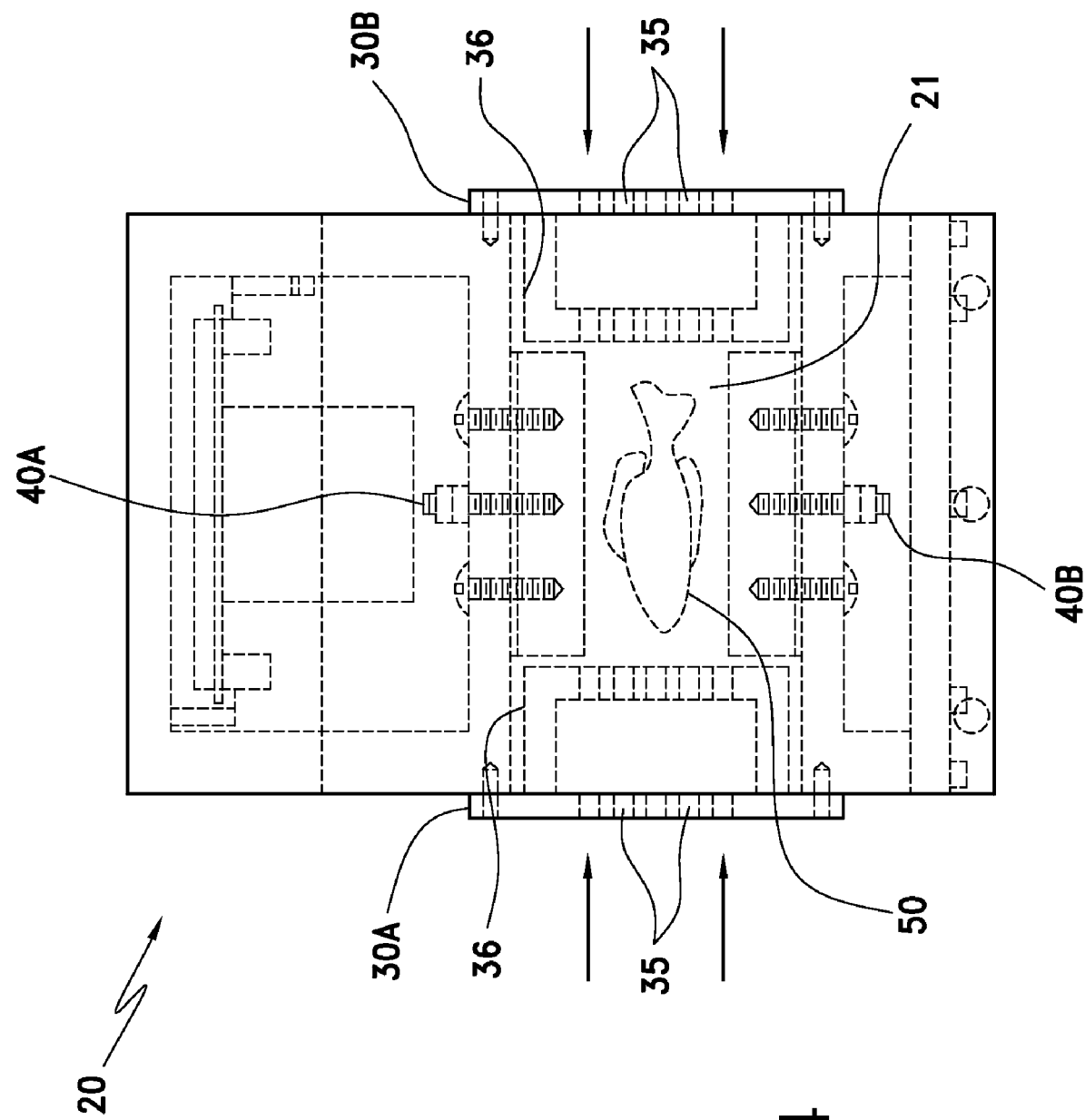
FIG. 4 is a side view of an individual aquatic species chamber cell or holding pen of the submersible chamber of FIG. 1.

FIGS. 1 and 2 depict a presently preferred configuration of the submersible chamber 10 of the in situ biomonitoring system of the present invention. As depicted in FIGS. 1 and 2, the submersible chamber 10 has a generally rectangular parallelpiped, or "box" shape, and includes eight separate holding cells or pens 20. The exact shape of the chamber 10 and number of pens 20 is not critical to the invention and should not be deemed to limit the scope of the invention. As best discerned from viewing FIGS. 1, 2 and 3 together, each separate holding cell 20 is generally configured as a rectangular tube. By tube, it is intended to convey that the lengthwise direction of the cell is significantly longer than the vertical cross-section. This tubular configuration of the cell 20 defines an interior space 21 for holding an aquatic species 50 as depicted in FIG. 3. The dimensions of the tube can be sized and manipulated to house an aquatic organism in a manner that provides for it to behave as if un-incarcerated to ensure it is not stressed due to its confinement (resulting in non-water quality based stress signals) and to ensure that reliable signals can be received and interpreted by the architecture described more fully below.

The present inventors had also considered and tested round tubular pens, but ultimately determined that their best mode for achieving reliable signals was through a generally rectangular box configuration. While round pens should not be deemed outside the scope of the invention, it is presently preferred to employ rectangular pens having top and bottom widths 22A, 22B narrower than the right and left sides 23A, 23B of the cell 20. As shown in the front view of FIG. 1, this may be described as being a "narrow" rectangular cell due to the lack of horizontal room for the organism to move to its left or right. When using freshwater blue gill as the aquatic organism 50, presently it is preferred that the cells be 6.75 inches in length and used in conjunction with electrodes that are 3.625 inches long.

In addition to the dimensions of the cells 20, another feature of the cells 20 that holds the aquatic organism 50 in a desired orientation is the provision of front and back end caps 30A, 30B. In general, the end caps 30A, 30B serve to not only prevent the aquatic organism 50 from escaping its cell, but to hold the organism in an area between the monitoring electrodes 40A, 40B. To this end, the end caps 30A, 30B each include an inwardly protruding section 36. These sections 36 serve as plugs or stops to hold the aquatic organism 50 in the central area 21 of the cell 20. This positioning is done to ensure the organism 50 remains disposed in an area between a top electrode 40A and a bottom electrode 40B.

The end caps include openings or channels 35 sized to permit the inflow and outflow of water. Preferably, these openings are sized to prevent the aquatic organism from escaping, protecting it from predators, while allowing water to flow through the cell 20 in a manner that is closely akin to the natural current in the body of water being monitored. With the presently preferred cell configuration, each end cap includes eight round channels 35 of a suitable diameter disposed as two vertical rows of four openings. This configuration is believed suitable to prevent vortexing or disruption of the flow of water along the length of the cell while ensuring the water does not stagnate, thereby assuring that the ambient water conditions are maintained inside the cells 20 throughout the monitoring process.

The electrodes 40A, 40B disposed on the top and bottom of each cell are used to capture physiological signals of the aquatic organism. The signals picked up by the electrodes, referred to as "ventilatory signals," are in analog form. The terms "ventilatory signal" and "ventilatory parameter" as used herein include data representative of body movement other than the movement of opercular flaps. Such non-opercular movement could, for example, include data resulting from an erratic episode due to sudden movement of the aquatic organism 50 within the chamber 10 or its cell 20. Again, presently preferred for use in connection with the present invention are cells having a length of 6.75 inches given use of electrodes that are about 3.625 inches long. Although not wishing to be bound by theory, it is believed that the use of chambers shorter than 6.75 inches can lead to cross-talk on adjacent electrodes. This is most probably a simple function of distance between two adjacent chambers and making sure that electrically conductive pathways do not exist between adjacent electrodes. It is also assumed that the amplitude of the cross-talk is a function of the water conductivity, the power of the electrical signal generated, amplification levels of the signal, and possibly the shape and configuration of the chamber. As previously mentioned, tubular chambers were somewhat problematic in early testing.

To maximize usefulness, the electrodes and associated wiring and electrical connections are preferably made from a corrosion resistant material or other material suitable for use in the intended environment. The electrodes may be made of a wide variety of materials, such as stainless steel. However, in some situations, metal electrodes may undergo galvanic interactions with water when the water has a high conductivity on the order of 4720 µS/cm or above (occurring, for example, with a salinity level of approximately 3 ppt), resulting in increased noise and signal instability. In such situations, it may be preferable to employ a nonmetallic material, such as graphite, for the electrodes.

The electrodes, their connections, the supporting components, and ultimate assembly to be used in an in situ system of the type described herein are well within the ability of one of ordinary skill in the art armed with the present specification. Suitable electrode assemblies may be those described by the present inventors previously in U.S. Ser. No. 10/774,639, filed Feb. 3, 2004, now U.S. Pat. No. 6,988,394, the entire contents of which are hereby incorporated by reference.

Ultimately, the electrodes 40A, 40B of one or more of the chambers communicates with a pre-amplifier 60. As best shown in FIG. 1, a pre-amplifier 60 is preferably configured to be a submersible amplifier that may be positioned in the chamber 10 above the cells 20 and submersed in situ along with the rest of the chamber 10. The ability to configure a pre-amplifier in communication with the electrodes and suitable for deployment with the chamber is within the ability of one of ordinary skill in the art and will not be further elaborated on herein. The pre-amplifier 60 serves to collect and amplifier the signals coming from the electrodes to a quality sufficient for communication to a land-based amplifier 70 or other receiver for further processing.

Speaking of signal quality, it is worth repeating that the aquatic organism holding cells 20 are made of a di-electric material, such as plastic and other non-conducting materials that are generally impervious to water or the environment to which the chamber is to be exposed. The present inventors have discovered that the use of a di-electric material greatly reduces cross-talk between the various cells and other interferences that had previously led other prior artisans to abandon the hope of every deploying a biomonitoring chamber in situ. The present inventors also discovered that, quite unexpectedly, the dielectric chamber helps to improve the signal strength or amplitude of the electrical signals that are picked u by the electrodes.

To be more specific, the inventors experimented with a submersible chamber with an open mesh architecture to best simulate ambient aquatic conditions. However, the open mesh configuration resulted in about an 85% reduction in signal strength when compared to the non-submersible fish chamber they described in U.S. Ser. No. 10/774,639, filed Feb. 3, 2004, now U.S. Pat. No. 6,988,394. While the inventors determined that an open mesh architecture could work, it would require far more amplification and suffers from much cross-talk. These drawbacks are exactly the types of signal quality reduction that has led many prior artisans away from pursuing the possibility of using a submersible biomonitoring chamber for monitoring water quality in situ.

The inventors then discovered that by placing dielectric shields (e.g., plastic pieces) on each side of the chamber resulted in only a 66% reduction in signal strength. Further refinement of this process yielded the presently preferred embodiment of a closed tubular chamber system which yields less than a 30% reduction in signal strength. Again, the exact phenomena that allows this strength of signal to be received is not well understood and unnecessary to understand to enable use of the present invention. The remarkable and unexpected results of the present invention speak for themselves in view of the incredulity of prior artisans when it comes to submersible biomonitoring chambers.

Figure 5:
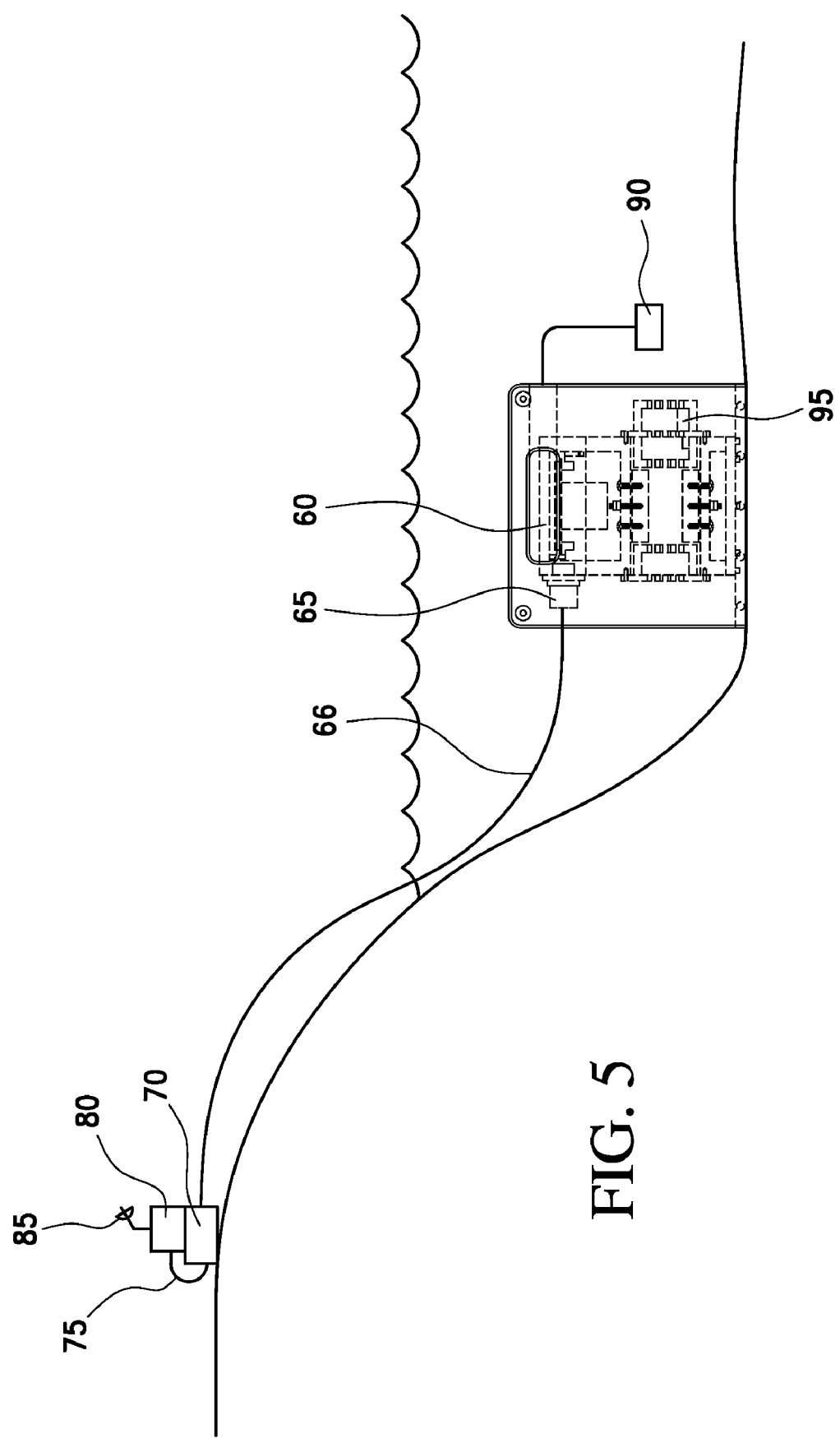
FIG. 5 is a diagram showing the various submersible and land-based components of an embodiment of the submersible in situ biomonitoring system of the present invention after deployment.

Turning back to the figures, once analog signals are received and processed in the pre-amplifier they are communicated to the land-based architecture for further processing, manipulation, or communication. To this end, as depicted in FIGS. 3 and 5, an umbilical jack 65 is provided with the pre-amplifier 60. The jack 65 is configured to accept an umbilical tether 66 of insulated coaxial cable (or other suitable material) that carries the signals from the submersed pre-amplifier to the land-based architecture.

According to a presently preferred embodiment, as depicted in the diagram of FIG. 5, the tether 66 carries the signals to a land-based amplifier 70. The land-based amplifier 70 takes the analog signals and preferably provides further filtering, processing, or amplification so suitable signals may be communicated to additional architecture to decipher water quality. In this embodiment, the analog signals are communicated via signal cables 75 to controller 80.

According to this embodiment of the invention, the controller 80 or a similar device is used to convert the analog electrical signals to digital signals, to further amplify and filter the signals, and to perform an analysis to determine ventilatory and body movement parameters, such as ventilatory rate, cough rate, average depth, and percent whole body movement. These parameters are continuously monitored and compared to previously measured data, control fish data, or both to determine the present physiological stress level of the aquatic species being monitored. How these signals are ultimately used in biomonitoring water quality is fully described by the present inventors previously in U.S. Ser. No. 10/774,639, filed Feb. 3, 2004, now U.S. Pat. No. 6,988,394, the entire contents of which are hereby incorporated by reference. Particular reference is made to the example set forth from column 11, line 20 through column 19, line 33 and the referenced figures.

The system also preferably includes a communication device 85 configured to allow information, results, and/or instructions to be remotely communicated to a command center or other receivers used for monitoring, tracking or remediating incidents affecting water quality.

As depicted on FIG. 5, the present invention may also be operatively deployed with a water quality sensor 90 and other prior art monitoring devices to be used in monitoring water quality as described in U.S. Pat. No. 6,988,394. While not explicated herein, one of ordinary skill in the art will readily appreciate the ability to use the features of the land-based monitoring systems discussed in U.S. Pat. No. 6,988,394 in connection with the present invention to monitor the desired parameters of a body of water and should be deemed to be within the scope of the present invention.

An additional feature depicted in FIG. 5 is the use of an aerator 95 to provide oxygen to the holding pens to aid the survival of their occupants in the event of an emergency. Any suitable prior art means for actuating the aerator in response to emergency conditions may be used with the present invention.

While the present specification has been written to highlight the discovery of how to make a biomonitoring system submersible for use in situ, one of ordinary skill in the art will appreciate the various features, operations, control systems, and other components disclosed in U.S. Pat. No. 6,988,394 are equally applicable in using the present invention to monitor and respond to changes in water quality. Furthermore, although shown and described is what is believed to be the most practical and preferred embodiments of the in situ components of the invention, it is apparent that departures from specific designs and methods described and shown will suggest themselves to those skilled in the art and may be used without departing from the spirit and scope of the invention. Accordingly, the present invention is not restricted to the particular constructions described and illustrated, but should be constructed to cohere with all modifications that may fall within the scope of the appended claims.

We claim:

1. A system for monitoring and evaluating water quality using ventilatory behavior and body movement of an aquatic organism in situ, comprising:
   a submersible chamber, said chamber being submersed in a body of water to be monitored and including a plurality of holding cells for housing said aquatic organism in situ, said holding cells comprising a di-electric material,
   at least one electrode disposed in said submersed chamber for receiving and transmitting electrical signals expressed by said aquatic organism in situ,
   a pre-amplifier disposed in said submersed chamber and in communication with said at least one electrode for receiving said electrical signals and amplifying said electrical signals,
   a tether in communication with said pre-amplifier on a first submersed end and in communication with a land-based receiver on a second end, whereby amplified signals from said pre-amplifier are communicated to said receiver, and
   a processor for processing said amplified signals to determine water quality.

2. The system of claim 1, wherein said holding cells comprise plastic.

3. The system of claim 1, wherein said chamber includes eight holding cells having a length of about 6.75 inches.

4. The system of claim 3, wherein said cells each include a respective front end cap and back end cap, said end caps configured to hold said aquatic organism adjacent said at least one electrode.

5. The system of claim 4, wherein said end caps include passages that allow water to flow through the cells without stagnation.

6. The system of claim 1, wherein said receiver comprises a land-based amplifier for amplifying said signal prior to communication with said processor.

7. The system of claim 1, wherein said processor compares initial respiratory data of said aquatic organism with subsequent data communicated from said amplifier to determine when said organism suffers physiological stress from the water being monitored.

8. The system of claim 7, further comprising a controller, said controller including said processor, wherein said controller initiates an alarm in response to a determination of physiological stress.

9. The system of claim 8, further comprising a water quality sensor in communication with said controller for providing additional water quality data to be analyzed by said processor.

10. A method of monitoring a body of water comprising:
    deploying a plurality of the systems of claim 1 in different areas of the body of water,
    monitoring by said systems to determine if one or more moitored water in a vicinity of each os said systems is causing physiological stress to aquatic organisms, and
    determining an area of exposure or path of exposure based on identification of locations and times the physiological stress is determined by said systems.

* * * * *